United States Patent [19]

Fong et al.

[11] Patent Number: 4,814,110
[45] Date of Patent: Mar. 21, 1989

[54] METHOD FOR ESTERIFYING DIHYDROXYBENZENES

[75] Inventors: Ronald A. Fong, Modesto; Richard R. Rowland, Danville, both of Calif.

[73] Assignee: The Clorox Company, Oakland, Calif.

[21] Appl. No.: 883,626

[22] Filed: Jul. 9, 1986

Related U.S. Application Data

[63] Continuation-in-part of Ser. No. 681,983, Dec. 14, 1984.

[51] Int. Cl.$^4$ .................. C07C 67/8; C07C 69/17
[52] U.S. Cl. .................... 260/400; 260/40/; 260/410.5; 560/142; 560/144
[58] Field of Search ............... 560/144, 142; 260/400, 260/404, 410.5

[56] References Cited

U.S. PATENT DOCUMENTS

| | | | |
|---|---|---|---|
| 2,082,790 | 6/1937 | Cherry | 260/99.40 |
| 2,345,006 | 3/1944 | Ross et al. | 260/410.5 |
| 2,815,365 | 12/1957 | Senkbeil et al. | 560/144 |
| 2,815,366 | 12/1957 | Senkbeil | 560/144 |
| 3,336,349 | 8/1967 | Voris | 560/144 |
| 3,462,468 | 8/1969 | Taylor et al. | 260/410.5 |
| 3,542,852 | 11/1970 | Selwitz | 260/476 |
| 3,624,135 | 11/1971 | Kablaoui | 260/479 R |
| 3,624,136 | 11/1971 | Kablaoui | 260/479 R |
| 3,631,227 | 12/1971 | Kablaoui et al. | 260/479 R |
| 3,822,114 | 7/1974 | Montgomery | 8/111 |
| 3,969,383 | 7/1976 | Dexter et al. | 260/410.5 |
| 4,036,773 | 7/1977 | Okorodudu | 252/56 R |
| 4,412,934 | 11/1983 | Chung et al. | 252/186.38 |
| 4,428,965 | 1/1984 | Elsohly et al. | 560/144 |
| 4,444,674 | 4/1984 | Gray | 252/95 |
| 4,473,588 | 9/1984 | Wilson et al. | 560/144 |
| 4,478,754 | 10/1984 | Kong-Chan | 560/130 |
| 4,613,332 | 9/1986 | Casella et al. | 252/186.38 |
| 4,727,182 | 2/1988 | Ratton | 560/144 |

FOREIGN PATENT DOCUMENTS

| | | |
|---|---|---|
| 0105672 | 4/1984 | European Pat. Off. . |
| 0105673 | 4/1984 | European Pat. Off. . |
| 060092 | 7/1985 | European Pat. Off. . |
| 2038522 | 2/1971 | Fed. Rep. of Germany . |
| 1375960 | 9/1964 | France . |
| 864798 | 4/1961 | United Kingdom . |
| 1316739 | 5/1973 | United Kingdom . |
| 2073197 | 10/1981 | United Kingdom . |

OTHER PUBLICATIONS

"Ketone Activated Potassium Monopersulfate Bleach," Chemicals Technical Service Report, American Potash & Chemical Corporation, Feb. 1, 1970.

*Encyclopedia of Chemical Technology*, 3rd ed., vol. 13, John Wiley & Sons, pp. 39–69 (1981).

Johnston, "Preparation of Hydroquinone Monoacetate," *Chemistry & Industry* (London) (24), 1000 (1982).

*Primary Examiner*—Edward A. Miller
*Attorney, Agent, or Firm*—Majestic, Parsons, Siebert & Hsue

[57] ABSTRACT

The present invention provides a method of esterifying dihydroxybenzene starting materials to synthesize unsymmetrical diesters in high yield. Many of the resultant unsymmetrical diesters are useful in dry bleaching compositions. The method can be practiced by selectively monoacylating a dihydroxybenzene starting material with an acid anhydride to form an intermediate monoester having the structure

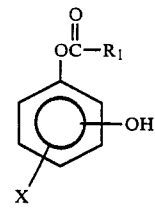

which is then acylated to form a diester reaction product having the structure

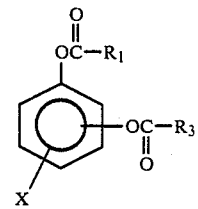

wherein $R_1$ is greater than $R_3$ (and both $R_1$ and $R_3$ are alkyl groups) and X is a substituent group which does not participate in the esterification (or which can have a protecting group thereon).

8 Claims, No Drawings

METHOD FOR ESTERIFYING DIHYDROXYBENZENES

This application is a continuation-in-part of Ser. No. 681,983, filed Dec. 14, 1984, entitled "Phenylene Mono- and Di-Ester Peracid Precursors," inventors Fong, et al., of common assignment herewith.

FIELD OF THE INVENTION

The present invention generally relates to a method for esterifying dihydroxybenzenes to synthesize unsymmetrical diesters therefrom via the selective formation of dihydroxybenzene monoesters.

BACKGROUND OF THE INVENTION

Peroxygen bleaching compounds are useful for bleaching fabrics, textiles and other materials, but are less effective than could be desired when bleaching temperatures less than 70° C. are utilized. Thus, peroxygen bleaching compositions desirably include activators, particularly for monopersulfate and monoperphosphate systems generating hypochlorite, in order to provide effective concentration of the bleaching agent under cooler wash temperature conditions.

In a technical service report dated Feb. 1, 1970 by American Potash & Chemical Corporation, it was reported that certain ketones (i.e. acetone, methyl ethyl ketone, methyl isobutyl ketone and cyclohexanone), activate persulfate bleaches in the presence of an alkaline buffer providing a pH of at least 8. U.S. Pat. No. 3,822,114, inventor Montgomery, issued July 2, 1974 discloses pyroxygen bleaching compositions which include a peroxygen bleaching compound, such as water-soluble monopersulfates and monoperoxy phosphates, and an aldehyde or ketone activator compound for the peroxygen compound. The aldehydes or ketones disclosed are said to activate the peroxygen compounds in aqueous solution having a pH of about 7 to about 12, and a preferred embodiment includes the optional addition of a water-soluble chloride salt to yield hypochlorite type bleaching.

Dry bleaching compositions, particularly useful for low temperature applications, are described in U.S. patent application Ser. No. 629,695, filed July 11, 1984, entitled "CONTROLLED GENERATION HYPOCHLORITE COMPOSITIONS AND METHOD," inventors Casella, et al., of common assignment herewith, in which generation of hypochlorite by reaction between a peroxygen bleaching agent and a chloride salt is promoted by an activator, preferably an aromatic diol in ester form having the structure illustrated below:

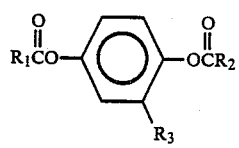

wherein one of $R_1$ and $R_2$ is an alkyl group having at least one to about eight carbon atoms, the other is hydrogen or an alkyl group having at least one to about eight carbon atoms, and $R_3$, if present, may be a substituent such as sulfonate, carboxylate, alkyl ethoxylate, quarternary ammonium or lower alkyl (e.g., methyl, ethyl or butyl).

As noted by D. Johnston, *Chemistry & Industry* 24, 1000 (1982), attempts to mono-derivatize benzene diols usually lead to a mixture of the unreacted difunctional compounds, the mono-substituted product and the bis-derivatized by-product. Johnston describes a procedure giving good yields of hydroquinone monoacetate from hydroquinone by reacting the hydroquinone with acetic anhydride in an equimolar ratio.

However, attempts to adapt the Johnston method to resorcinol by reaction with longer chain acid anhydrides have been found to produce disappointing yields of monoester and have favored formation of symmetrical diesters.

SUMMARY OF THE INVENTION

It is an object of the present invention to provide a method for selectively monoacylating dihydroxybenzenes with improved yields. It is a further object of the present invention to provide a method by which excellent yields of unsymmetrical diesters of dihydroxybenzenes may be obtained.

In one aspect of the present invention, monoesters of dihydroxybenzenes can be selectively formed by reacting dihydroxybenzene starting material with an acid anhydride where the dihydroxybenzene is in a molar excess, and preferably the molar ratio of dihydroxybenzene starting material with respect to the acid anhydride is at least about 1.5:1.

Another aspect of the present invention is a method for the sequential esterification of dihydroxybenzenes to synthesize unsymmetrial diesters therefrom. The dihydroxybenzene starting material is selectively monoacylated with an acid anhydride to form an intermediate monoester, which is then acylated to form the unsymmetrical diester reaction product. Any carboxylic acid by-product is preferably removed by base extraction from the intermediate monoester, and yields of an unsymmetrical diester reaction product on the order of about 80% may be achieved.

DETAILED DESCRIPTION OF THE PREFERRED EMBODIMENTS

This invention generally relates to a method of making peracid precursors from dihydroxybenzene starting materials, preferably via an intermediate monoester of the dihydroxybenzene. Peracid precursors are usefully combined with a source of peroxygen (and optionally a halide salt) to promote good bleaching, particularly in wash temperatures below 70° C. The peracid precursors include monoesters (having the general structure illustrated by Formula 1, below) and phenylene diesters (having the general structure illustrated by Formula 2, below).

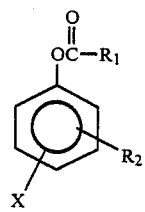

Formula 1

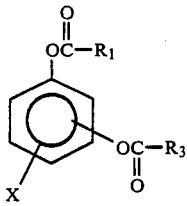

Formula 2

Particularly useful peracid precursors in the monoester form preferably are wherein $R_2$ is hydroxyl and $R_1$ is an alkyl of about 1 to about 20 carbons, more preferably 1 to 15, and most preferably 1 to 11 carbons. The latter in particular appears to provide surface active peracids when combined with a hydrogen peroxide source in aqueous solution.

The diesters are wherein $R_3$ is preferably 1 to 20, more preferably 1 to 15, and most preferably 1 to 11 carbons. The compounds are mixed (that is, are unsymmetrical) diesters when $R_1$ and $R_2$ are unequal.

When either $R_1$ or $R_3$ is less than five carbons and the other greater, it is believed that both hydrophobic and hydrophilic peracids are generated. Therefore, if used in aqueous media with a source of hydrogen peroxide (e.g., sodium perborate monohydrate), for example as an all-fabric bleach, two different oxidizing species appear to be present which then attach to hydrophilic soil, such as tea and wine, and oily soils, such as sebum.

For example, it is believed that when one of the ester functionalities has an alkyl straight chain length of less than 5, e.g., wherein $R_1$ or $R_3$ is $CH_3$, and the other alkyl group's chain length is greater than 5 carbon atoms, peroxyacids which are, respectively, hydrophilic and hydrophobic are generated. It is believed that particulate soils and hydrophilic stains can be attacked with a hydrophilic peroxyacid bleach while oily soils can be attacked with a hydrophobic peroxyacid bleach. Different pre-formed hydrophobic and hydrophilic peroxyacid bleaches were combined in published European patent application EP No. 68547, whose disclosure is incorporated herein by reference. Pre-formed peracids appear, however, to have storage stability problems and may lose significant amounts of active oxygen (A. O.) upon prolonged storage.

The dihydroxybenzenes are weak acids with two disassociation constants. They are generally classified as antioxidant agents and are useful analytical reagents. Their structures, uses and chemistries are more thoroughly explored in Kirk-Othmer, *Encyclopedia of Chemical Technology*, 3rd Ed., Vol. 13, pages 39–69 (1981), which pages are incorporated herein by reference. Among the dihydroxybenzenes which are useful as starting materials in accordance with the present invention are hydroquinone, resorcinol and catechol.

Hydroquinone (1,4-benzenediol; 1,4-dihydroxybenzene; p-dihydroxybenzene) is a white crystalline compound which can be obtained by dry distillation of quinic acid or by reduction of quinone.

Resorcinol (1,3-benzenediol; 1,3-dihydroxybenzene; m-dihydroxybenzene) is a crystalline compound with a faint aromatic odor, and a sweet/bitter taste. It may be produced by the alkali fusion of galbanum and asafetida resins.

Catechol (1,2-benzenediol; 1,2-dihydroxybenzene; o-dihydroxybenzene) is a crystalline compound with a phenolic odor and a sweet and bitter taste. It may be obtained by dried distillation of catechin which is found in the aqueous extract of catechu, which is an extract of an East Asian acacia plant.

Useful dihydroxybenzene starting materials include those where the aromatic ring has substituents thereon, and substituted phenylene diesters have been found to be particularly effective in low temperature bleaching applications. Solubility and dispersibility (and hence performance) can be improved by the addition of solubilizing groups placed on the aromatic ring. Thus, X of Formulas 1 and 2, above, represents substituents.

Nitro groups can be substituted on the aromatic ring, for example, when the dihydroxybenzene is reacted with nitric acid in the presence of sulfuric acid. Sulfonate groups can be substituted when the dihydroxybenzene is reacted with concentrated sulfuric acid. Ammination will generally be produced by reacting a source of amino with the dihydroxybenzene in the presence of liquid ammonia. Sulfonate or carboxylate groups are especially preferred as solubilizing groups for the peracid precursors.

A number of substituted dihydroxybenzenes are known and commercially available, and suitable dihydroxybenzene starting materials used in practice of the present invention have the structure already shown by Formula 1, where $R_2$ is hydroxyl and X can be a wide variety of substituents such as sulfonate, halide, benzylamino, amino, alkyl ethoxylate, quarternary ammonium and carboxylate. For substituent groups which may be sensitive to acylation, such as amino substitutents, it is generally desirable to utilize a protecting group during practice of the invention, whereby the protecting group can subsequently be removed. On an amine group, for example, bulky substituents such as alkyl chains could be present.

The X substituent, if present, is preferably in the 5 position on the ring of resorcinol and in the 4 or 5 position on the ring of catechol. Ortho substituents, at the 2 position of the hydroquinone ring, at the 2 position of resorcinol or the 6 position of catechol are less desirable, particularly with bulky groups, as the acylation of the adjacent hydroxyl is inhibited.

It has been found that peracid precursors containing unsymmetrical esters provide extremely good bleaching and can be incorporated into a liquid or solid matrix for use in liquid or solid detergent bleaches or laundry aids. These peracid precursors can desirably be prepared by practice of the present invention and have the structure already shown by Formula 2.

Particularly preferred peracid precursors are where one ester is an acetate (e.g., $R_1$ is $-CH_3$) and the other is an hexanoate, heptanoate, octanoate or nonanoate (e.g., $R_3$ is $-(CH_2)_4CH_3$ to $-(CH_2)_7CH_3$). In preferred bleaching composition embodiments, the total number of backbone carbons of $R_1$ plus $R_3$ should be in the range of 2-20, more preferably 5-20, most preferably 7-14.

For example, a bleach composition is provided with a monoester having the following ingredients:

| | |
|---|---|
| 15.5% | Sodium Perborate Monohydrate |
| 11.9% | Resorcinol Monooctanoate |
| 7.0% | Nonionic Surfactant |
| 15.0% | Sodium Carbonate |
| 50.6% | Sodium Sulfate |
| 100.0% | |

The above composition including monoester is formulated to deliver, desirably, 14 parts per million total available oxygen (ppm A. O.), at a pH of about 10.5.

When a diester compound is the acid precursor, another bleach composition has the following ingredients:

| | |
|---|---|
| 15.5% | Sodium Perborate Monohydrate |
| 7.0% | Resorcinol Octanoate Acetate |
| 7.0% | Nonionic Surfactant |
| 15.0% | Sodium Carbonate |
| 55.5% | Sodium Sulfate |
| 100.0% | |

The above composition including unsymmetrical diester is formulated to deliver, desirably, about 14 ppm A. O. at a pH of about 10.5.

Other peroxygen sources, such as sodium perborate tertrahydrate or sodium percarbonate, are suitable in bleaching compositions utilizing peracid precursors made in accordance with the present invention. If a more detergent-type product is desired, the amount of filler can be increased and the precursor halved or further decreased.

Unsymmetrical diesters from dihydroxybenzene starting materials could be used with a peroxygen bleaching agent and a chloride salt, in bleaching compositions such as are described in previously noted U.S. patent application Ser. No. 629,695, filed July 11, 1984. The formation of hypochlorite is delayed in that the ester moieties of the dihydroxybenzene first hydrolyze to hydroxyl groups, but once hydrolyzed the resultant activator then promotes, or catalyzes, reaction between the peroxygen bleaching agent and chloride salt.

However, by varying the amount and form of activator precursor, the amount of peroxygen bleaching agent, and the amount of chloride salt, a wide range of hypochlorite generation concentrations and delay profiles may be obtained, if desired.

Suitable such bleaching compositions have from about 5 wt % to about 80 wt. % peroxygen bleaching agent, from about 10 wt. % to about 70 wt. % of the halide salt, and from about 0.1 wt. % to about 10 wt. % of the activator precursor. More preferably, the peroxygen bleaching agent is from about 25 wt. % to about 65 wt. %, the alkali halide salt from about 35 wt. % to about 45 wt. %, and the activator or activator precursor from about 0.5 wt. % to about 2 wt. %.

A buffering agent is preferably present in an amount sufficient to maintain a pH within the range of from about 8 to about 11, more preferably from about 9 to about 10.5, when the compositions are dissolved in aqueous solutions. Such compositions may include other components for various purposes such as to aid in storage stability, to enhance or modify the solubilization rate of the activator precursor, in addition to including other well known laundry additives.

One aspect of the inventive method (sometimes hereinafter the "first embodiment") is the selective formation of dihydroxybenzene monoesters. Thus, a dihydroxybenzene, such as hydroquinone, resorcinol, or catechol, which may be substituted or unsubstituted, is initially provided as a starting material and is monoesterified by reaction with an acid anhydride. The reaction mixture of the reacting step is mildly exothermic and although mild amounts of heat are acceptable, the reaction mixture should not be subjected to excessive heat which can lead to transacylation. Preferably, the reaction is conducted at about room temperature.

It is very important that the dihydroxybenzene starting material be in a molar excess with respect to the acid anhydride, and preferably the reaction is wherein the dihydroxybenzene starting material with respect to acid anhydride is in a molar ratio of at least about 1.5:1. The reaction of dihydroxybenzene starting material with acid anhydride at the molar excess of dihydroxybenzene starting material monoacylates the starting material to form the monoester reaction product which is recoverable in yields of greater than about 50% (that is, the starting material is selectively monoacylated). Use of molar ratios increasing above 1.5:1 and up to about 5:1 or 6:1 enhances the selectivity of the reaction; however, molar ratios of greater than about 6:1 dihydroxybenzene starting material to acid anhydride tend not to increase selectivity much further and are less practical. A particularly preferred range of molar ratio for dihydroxybenzene starting material to acid anhydride is about 3:1 to about 6:1.

The reaction may be acid or base catalyzed. Suitable acid catalysts include, for example, sulfuric acid, toluene sulfonic acid, methane sulfonic acid, trichloroacetic acid, and trifluoroacetic acid. Suitable basic catalysts include 4-dimethylaminopyridine, triethylamine, sodium carbonate, sodium bicarbonate, tetramethylpiperidine; generally, any tertiary amine or weakly basic catalyst can be used. The reaction may be conducted over (and catalyzed by) a basic or acidic ion exchange resin (well known to the art), such as one of the Dowex resins (available from Dow Chemical Company).

The reaction mixture of the reacting step preferably is solubilized, or in liquid form. Suitable solvents for use to ensure that all reaction components are maintained in the liquid phase are non-nucleophilic to avoid interference with the course of the esterification reaction, and are preferably low molecular weight, volatile ketones (such as acetone) or halogenated hydrocarbons (such as chloroform). The monoesterified, reaction product resulting from practice of the first embodiment has the structure previously illustrated and described as Formula 1.

In another aspect of the inventive method (sometimes hereinafter the "second embodiment"), the sequential esterification of dihydroxybenzenes to synthesize unsymmetrical diesters therefrom is provided. In accordance with the second embodiment, a dihydroxybenzene starting material is selectively monoacylated with a first acid anhydride to form an intermediate monoester. The selective monoacylating step is preferably carried out by reacting the dihydroxybenzene starting material with the first acid anhydride at about ambient temperature, with the dihydroxybenzene starting material being in a molar excess and having a molar ratio with respect to the acid anhydride of at least about 1.5:1.

That is, the sequential esterification method of the present invention preferably begins by utilizing the previously described first embodiment of the invention and then continues by removing any carboxylic acid by-product from the resultant intermediate monoester. For example, octanoic acid will be an acid by-product if octanoic anhydride is the acid anhydride used in the initial, monoesterification.

Removing any carboxylic acid by-product from the intermediate monoester may be done by base extraction (such as with sodium carbonate) and prevents the formation of a "mixed" anhydride in the reaction mixture. The presence of carboxylic acid by-product in the subsequent acylation step is undesirable, as it has been found to increase the amount of symmetrical di-ester formed. Thus, removal of carboxylic acid byproduct is important for selectivity. Although some symmetrical diester is formed during the formation of intermediate monoester, the quantities formed are low (since the monoacylation is selective) and the small amount of symmetrical diester does not need to be removed in order to practice the second embodiment in obtaining high yields of unsymmetrical diester of dihydroxybenzene.

Practice of the second embodiment method further continues with the intermediate monoester (from which any carboxylic acid by-product and any unreacted dihydroxybenzene starting material have been removed) which is then acylated with a second acid anhydride to form an unsymmetrical diester reaction product. The unsymmetrical diester reaction product has the structure previously illustrated and described as Formula 2.

In practice of the second embodiment, the first acid anhydride chosen with which to monoacylate the dihydroxybenzene starting material preferably is where $R_1$ is 5 to 12 carbons, where the first acid anhydride has the structure

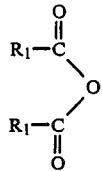

The second acid anhydride has the structure

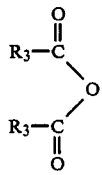

where $R_3$ of the second anhydride is less than $R_1$ of the first anhydride, more preferably where $R_3$ is a carbon chain from 1 to 4 carbons.

Initial formation of the longer chain ester has been found to be important in selectivity and hence yield. Practice of the inventive second embodiment can provide yields of unsymmetrical diester reaction product greater than about 80-85%.

Acylation of the second hydroxyl group on the intermediate monoester compound typically is conducted at about room temperature (albeit the reaction is mildly exothermic).

As with preparation of the intermediate monoester, acylation, that is esterification, of the second hydroxyl group may be acid or base catalyzed and, if desired, conducted in suitable solvents.

The following examples, methods, materials and results are described for purposes of illustrating the present invention. However, other aspects, advantages and modifications within the scope of the invention will be apparent to those skilled in the art to which the invention pertains.

As illustrated by comparative Example I, below, resorcinol monooctanoate was synthesized by an adaption of the previously described Johnston method for comparison with practice of the first embodiment in accordance with the invention. In the comparative synthesis of Example I, yields of the desired monoester (i.e., resorcinol monooctanoate) were typically only about 40 wt. % whereas the symmetrical diester was coproduced in slightly larger amount. That is, the comparative synthesis was not a selective monoacylation.

By contrast to the comparative synthesis, practice of the first embodiment, as illustrated by Example II, below, provides yields of about 80-95 wt. % resorcinol monooctanoate Example III illustrates practice of the first embodiment in accordance with the invention with another dihydroxybenzene starting material (i.e., catechol). Again, practice of the invention provides extremely high yields (90-95 wt. %) of the desired monoester.

EXAMPLE I

Comparative Synthesis of Resorcinol Monooctanoate

Resorcinol (2.75 g, 0.025 mole), 4-dimethylaminopyridine (0.3 g, 0.0025 mole), and triethylamine (2.5 g, 0.025 mole) were dissolved in 50 ml of ethyl acetate in a 100 ml round bottom flask equipped with a magnetic stir bar. Octanoic anhydride (6.76 g, 0.025 mole) was added dropwise, via an addition funnel, to the stirred solution over a 100 minute time period.

The resulting solution was stirred for an additional 30 minutes, at which time the solvent was removed via rotary vacuum evaporation. The remaining oil was dissolved in 200 ml of ethyl ether and extracted with a 200 ml portion of 3% HCl to remove the 4-dimethylaminopyridine catalyst, and four 100 ml portions of 5% $NaHCO_3$ were used to remove the octanoic acid by-product. After drying the organic phase with 40 grams of $Na_2SO_4$, the ether was removed by rotary vacuum evaporation and the remaining oil was redissolved in 15 ml of chloroform. The sample was then chromatographed in a column on 200 grams of silica gel G with chloroform/petroleum ether (1:2 vol/vol ratio) and pure resorcinol monooctanoate (2.36 g) was collected. Yields of the desired monoester were typically only about 40% (wt. Symmetrical diester, resorcinol dioctanoate, was co-produced in a slightly greater portion (about 50% (wt.)).

EXAMPLE II

Inventive Synthesis of resorcinol Monooctanoate

Resorcinol (13.76 g, 0.125 mole), 0.7 g 4-dimethylaminopyridine (0.68 g, 0.0057 mole), triethylamine (2.5 g, 0.025 mole) were dissolved in 50 ml of acetone in a 250 ml round bottom flask equipped with a magnetic stir bar. Octanoic anhydride (6.7 g, 0.025 mole) was dissolved in 15 ml of acetone and added dropwise, via an addition funnel, to the stirred solution over 10 minutes, the resulting pale yellow solution was stirred for an additional 1¾ hours, at which time the solvent was removed via rotary vacuum evaporation. The remaining oil was dissolved in 200 ml of ethyl ether and extracted one time with 200 ml of 3% HCl to remove the 4-dimethylaminopyridine catalyst and four times with 100 ml of 5% $NaHCO_3$ to remove octanoic acid. After drying the organic phase with 40 grams $Na_2SO_4$, the ether was removed by rotary vacuum evaporation and the oil redissolved in 100 ml of 1:1 (vol) of benzene/cyclohexane. Unreacted resorcinol was crystallized out after two hours at about 10° C. which was then removed by filtration. After one more wash with 5% NaHCO3, the solvent from the organic phase was removed by rotary vacuum evaporation to give 5.9 grams of resorcinol monooctanoate (90-95 wt. % yield).

EXAMPLE III

Inventive Synthesis of Catechol Monooctanoate

To a 50 ml round bottom flask was added catechol (Aldrich, 3.3 g, 30 mmols), octanoic anhydride (5.4 gms, 20 mmols) and 5 mls of ethyl ether. After all the catechol was dissolved, one drop of methane sulfonic acid was added and the solution stirred for two hours at room temperature. 30 mls of petroleum ether was then added and the unreacted catechol was crystallized at 5°-10° C. for one hour. Greater than 95% of the unreacted catechol was recovered. After filtration, the organic solution was washed three times with 50 mls of 5% NaHCO3 and the catechol monooctanoate (4.4 g) was isolated in 90-95 wt. % yield after rotary vacuum evaporation of the solvents.

Example IV, below, illustrates practice of the second embodiment of the present invention. As can be seen in Example IV, the resultant unsymmetrical diester reaction product was obtained in a yield of 82.5%.

EXAMPLE IV

Inventive Synthesis of Resorcinol Acetate Octanoate (A) Preparation of the monoester: Resorcinol (55.04 g, 0.50 mole), 4-dimethylaminopyridine (2.0 g, 0.016 mole) and triethylamine (10.1 g, 0.10 mole) were weighed into a 1 liter round bottom flask equipped with a magnetic stir bar and dissolved, with stirring, in 200 ml of acetone. Octanoic anhydride (27.0 g, 0.10 mole) was dissolved in 50 ml of acetone, placed in a 125 ml addition funnel and added dropwise to the stirred resorcinol/4-dimethylaminopyridine/triethylamine solution over 35 min. The reaction was then stirred an additional 1 hr. 40 min.

The solvent was removed by rotary evaporation (40° C.) leaving a thick oil. To this oil was added 150 ml of 40/60 (vol/vol) petroleum ether (bp. 30°-60° C.)/dichloromethane. After vigorous shaking, two phases separated upon standing.

The upper phase (solvent) was decanted, followed by three more extractions (150 ml each) of the lower phase with 40/60 petroleum ether/dichloromethane. The combined petroleum ether, dichloromethane extracts were themselves extracted with 1×250 ml 5% aqueous hydrochloric acid, 4×250 ml 7% aqueous sodium bicarbonate, and 1×250 ml filtered saturated sodium chloride solution. The organic phase was dried over 63 g sodium sulfate (anhydrous), filtered and rotary/evaporated (40° C.) to a light yellow oil. Drying in vacuo at room temperature yielded 22.8 g of oil containing resorcinol monooctanoate (82.5 wt. % yield) and a small amount of resorcinol dioctanoate (14.7 wt. %).

Unreacted resorcinol was recovered from the lower phase of the petroleum ether/dichloromethane extraction by dissolving in 250 ml of 20/80 (vol/vol) benzene/petroleum ether, and this was then extracted with 4×250 ml of 5% aqueous sodium bicarbonate. The combined aqueous extracts were acidified to pH 2 of concentrated hydrochloric acid extracted with 4×300 ml dichloromethane. The combined organic extracts were dried over sodium sulfate, filtered, and rotary-evaporated to an oil (44 g) which crystallized upon standing. Filtration and washing with petroleum ether followed by drying yielded 37 g (about 87 wt. %) of recovered resorcinol.

(B) Preparation of the unsymmetrical diester via the monoester: To 22.7 g of the resorcinol monooctanoate reaction product obtained in (A) above, was added acetic anhydride (20.3 g, 0.198 mole) and 3 drops methane sulfonic acid in a 500 ml round bottom flask with a magnetic stir bar. A slight warming was noted, and a color change from yellow to orange and back to yellow occurred within ½ hr. The reaction was stirred 2 hrs., then diluted with 400 ml 50/50 (vol/vol) pentane/ethyl ether and extracted with 4×250 ml of 7% aqueous sodium bicarbonate and 1×25 ml saturated sodium chloride solution. The organic phase was dried over 60 g sodium sulfate, filtered and rotary-evaporated to a light yellow oil. Vacuum drying gave 26.0 g of product which was determined to be resorcinol acetate octanoate (yield of 82.5 wt. %) and 14.7 wt. % resorcinol dioctanoate as by-product.

Examples V and VI, below, also illustrate practice of the invention's second embodiment. The "x" substituent of the Example V dihydroxybenzene starting material is carboxymethyl and of the Example VI starting material is chloride. Yields of the resultant unsymmetrical diester reaction products were about 71% and 75%, respectively.

EXAMPLE V (A) 16.81 g (0.10 mole) 3,5-dihydroxymethyl Benzoate, 0.4 g (0.003 mole) 4-DimethylaminoPyridine (DMAP), 2.02 g (0.02 mole) Triethyl Amine (TEA) and 60 ml acetone were combined in a 250 ml round bottom flask equipped with a magnetic stir bar and addition funnel. This was stirred until complete solution was obtained 5.4 g (0.02 mole) octanoic anhydride was placed in the addition funnel and added dropwise to the stirred phenol/amine solution over ½ hr. The reaction was stirred an additional 2½ hrs., then the solvent was stripped by rotary evaporation. The thick residual oil was extracted with 4×100 ml of 10% dichloromethane in hexane (vol/vol), with the last extraction going overnight. The combined extracts were themselves extracted with 4×200 ml 5% HCl and 8×200 ml 5% NaHCO3, dried over Na2SO4, and rotary evaporated to an oil which crystallized upon standing. Wt=6.0 g (5.9 g theoretical) IR ($_{OH}$ at 3420 cm$^{-1}$, $_{C=O}$ at 1765 cm$^{-1}$ and 1722 cm$^{-1}$) and TLC (CH2Cl2 on silica GF, $R_f$ about 0.18) indicates substantially one product as the desired intermediate, illustrated below. There was a minor amount of higher $R_f$ material, presumably the dioctanoate ester.

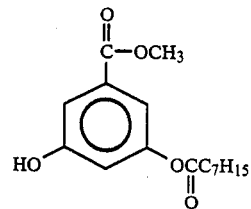

(B) The 6.0 g of oil from step (A) of the reaction was dissolved in 20 ml of diethyl ether. 3.0 g (0.029 mole) acetic anhydride and 3 drops methane sulfonic acid were added and the reaction was stirred for 3 hrs. At this time 250 ml diethyl ether was added and the reaction was washed with 4×100 ml of 5% NaHCO₃. The ether layer was dried over Na₂SO₄, filtered, and rotary evaporated to an oil (wt =5.5 g, 82% theo.). This material was shown by G.C. to be about 87% mixed ester (illustrated below) and 10% dioctanoate ester. IR and ¹³C-NMR confirm the structure of the compound as 3-acetoxy-5-octanoyl oxy-methyl benzoate.

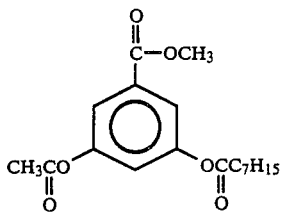

EXAMPLE VI (A) 14.75 g (0.10 mole) 4-Chloro resorcinol, 2.02 g (0.02 mole) Triethylamine, and 0.4 g 4-dimethyl aminopyridine (DMAP, 0.003 mole) were weighted into a 250 ml round bottom flask equipped with addition funnel and magnetic stir bar and dissolved in 60 ml of acetone. 5.4 g (0.02 mole) Octanoic anhydride in 5 ml of acetone was added dropwise over ½ hr. to the stirred resorcinol-/amine solution. The reaction was stirred an additional 2 hrs. and the solvent rotary evaporated. The oily residue was extracted with 2×150 ml 10% dichloromethane in hexane (vol/vol) and 1×75 ml Hexane. The combined organic extracts were washed with 3×200 ml of 5% NaHCO₃, 2×150 ml 5% HCl and 1×200 ml H₂O. After drying over sodium sulfate, and filtration, the solvent was rotary evaporated leaving a light yellow oil (wt =5.9 g, 5.4 g theoretical). IR ($\nu_{OH}$ at 3420 cm⁻¹, $\nu_{C=O}$ at 1740 cm⁻¹ and 1760 cm⁻¹ and TLC (20% CH₂Cl₂ in Hexane on silica gel GF) indicate the two products, illustrated below, with R$_f$'s of 0.08 and 0.17 along with a minor amount of the di-octanoyl oxy Resorcinol.

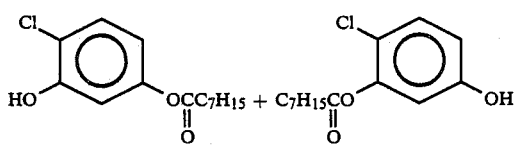

(B) To 5.9 g of product oil from step A of the reaction was added 3.08 (0.029 mole) acetic anhydride and 2 drops of methanesulfonic acid. This was stirred for 2 hrs., then diluted with 160 ml hexane and extracted with 5×100 ml 5% NaHCO₃ and 1×200 ml water. The organic layer was dried over sodium sulfate, filtered and rotary evaporated to an oil wt=5.0 g (80% wt). This oil was substantially one component by GLC (94%) with IR and ¹³C-NMR confirming the 4-Chloro resorcinol, acetate/octanoate mixed esters having the structures illustrated below.

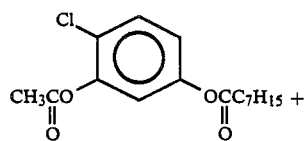

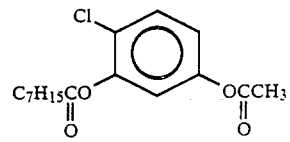

As previously described, molar ratio, temperature, the relative chain length of R₁ and R₃ for the first and second acid anhydrides, and the removal of carboxylic acid by-product are all believed to affect selectivity of the inventive method. This is illustrated by the following example.

Comparative Example VII, below, illustrates the loss of selectivity in the second embodiment process when the shorter chain acid anhydride is first used, rather than the longer, and the molar ratio of dihydroxybenzene starting material with respect to the first acid anhydride is about 1:1. Thus, yield of the unsymmetrical mixed ester (1-acetoxy-3-octanoyloxybenzene) was only about 47%.

COMPARATIVE EXAMPLE VII

To 5.5 g (50 mmole) of resorcinol in 100 ml of ethyl acetate was added 0.3 g (2.5 mmole) of 4-dimethylaminopyridine catalyst at room temperature. To this solution was added 5.1 g (50 mmole) of acetic anhydride while keeping the solution at 21° C. with an ice bath. The mixture was stirred for 60 min. and this was followed by the addition of 13.5 g (50 mmole) of octanoic anhydride. The solution was stirred for an additional 2 hrs. at room temperature, and then the solvent was removed under reduced pressure. The residue was redissolved in diethyl ether (100 ml) and washed three times with 50 ml of 5% sodium carbonate. The organic layer was separated, dried over sodium sulfate, filtered, and the solvent was then removed by rotary vacuum evaporation. The residue was then separated by chromatography on silica gel with chloroform/petroleum ether (1/1, V/V) to yield 6.6 g (47% yield, of the unsymmetrical mixed ester (I) and 3.75 g of resorcinol diacetate II.

During practice of the invention, the solvents, unreacted (and excess) dihydroxybenzene starting materials and carboxylic acid by-products are all recoverable and can be recycled. The course of the reactions, particularly the formation of diester reaction product in practice of the second embodiment, may be monitored by gas chromatography.

It is to be understood that while the invention has been described in conjunction with preferred specific embodiments, that the foregoing description as well as the examples, are intended to illustrate and not limit the scope of the invention, which is defined by the scope of the appended claims. Other aspects, advantages and modifications within the scope of the invention will be apparent to those skilled in the art to which the invention pertains.

We claim:
1. A method for the sequential estrification of dihydroxybenzenes to synthesize unsymmetrical diesters thereof comprising:
   selectively acylating a dihydroxybenzene starting material with a first acid anhydride to form an intermediate monoester having the structure

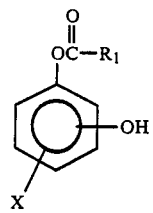

wherein $R_1$ is an alkyl of from about 5 to about 11 carbons and X is hydrogen or a substituent group, the dihydroxzybenzene starting material being in a molar ratio with respect to the first acid anhydride of at least about 3:1;

removing any carboxylic acid by-product and unreacted dihyroxybenzene starting material from the intermediate monoester; and, acylating the intermediate monoester to form an unsymmetrical diester reaction product having the structure

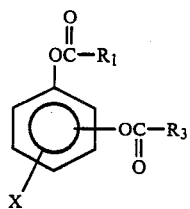

wherein $R_3$ is an alkyl having fewer carbons than $R_1$.

2. The method as in claim 1 wherein carboxylic acid by-product is removed by base extraction.

3. The method as in claim 1 wherein the first acid anydride has the structure

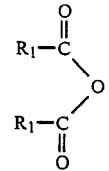

wherein $R_1$ is an alkyl of from about 5 to about 11 carbons.

4. The method as in claim 1 wherein the selective acylating of dihydroxybenzene starting material is conducted at about ambient temperature.

5. The method as in claim 1 wherein the selective acylating of dihydroxybenzene starting material is conducted in the presence of an acidic or a basic catalyst.

6. The method as in claim 4 wherein the unsymmetrical diester reaction product is recoverable in at least about 80% yield.

7. The method as in claim 1 wherein the acylating of intermediate monoester includes contacting said intermediate monoester with a second acid anhydride having the structure

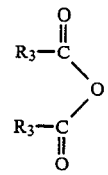

wherein $R_3$ is an alkyl having 1 to 4 carbons.

8. The method as in claim 1 wherein the dihydroxybenzene starting material is hydroquinone, substituted hydroquinone, catechol, substituted catechol, resorcinol or substituted resorcinol.

* * * * *